United States Patent [19]
Meier et al.

[11] Patent Number: 4,788,499
[45] Date of Patent: Nov. 29, 1988

[54] METHOD AND EDDY CURRENT TEST PROBE FOR THE INSPECTION OF SCREWS FOR NUCLEAR REACTOR PRESSURE VESSELS

[75] Inventors: Werner Meier, Erlangen; Edgar Friedrich, Möhrendorf; Erich Modlich, Forchheim, all of Fed. Rep. of Germany

[73] Assignee: Kraftwerk Union Aktiengesellschaft, Mülheim an der Ruhr, Fed. Rep. of Germany

[21] Appl. No.: 795,340

[22] Filed: Nov. 6, 1985

[30] Foreign Application Priority Data

Nov. 19, 1984 [DE] Fed. Rep. of Germany ....... 3442256

[51] Int. Cl.⁴ ..................... G01N 27/90; G21C 17/00
[52] U.S. Cl. .................................... 324/238; 324/240; 324/262
[58] Field of Search ............... 324/228, 234, 236–243, 324/217, 218, 262; 33/DIG. 1; 376/245, 249

[56] References Cited
U.S. PATENT DOCUMENTS

| 2,519,367 | 8/1950 | Gunn et al. | 324/240 |
| 2,958,818 | 11/1960 | Cowan et al. | 324/217 |
| 3,036,266 | 5/1962 | Hulls | 324/208 |
| 3,495,166 | 2/1970 | Lorenzi et al. | 324/238 |
| 3,939,404 | 2/1976 | Tait | 324/238 X |
| 4,547,962 | 10/1985 | de Walle et al. | 324/240 X |

FOREIGN PATENT DOCUMENTS

| 2817574 | 10/1979 | Fed. Rep. of Germany. | |
| 0110048 | 9/1981 | Japan | 324/238 |
| 748235 | 7/1980 | U.S.S.R. | 324/262 |

Primary Examiner—Gerard R. Strecker
Attorney, Agent, or Firm—Herbert L. Lerner; Laurence A. Greenberg

[57] ABSTRACT

A method for the inspection of screws with an eddy current test probe including an insulating material body having a linear contact surface and at least one coil disposed in the body, includes orienting the coil transverse to threads of a reactor pressure vessel setscrew to be inspected, feeding high-frequency alternative current through the at least one coil, generating a coil field covering at least two threads, and guiding the linear contact surface along the threads, and a device for carrying out the method.

11 Claims, 1 Drawing Sheet

METHOD AND EDDY CURRENT TEST PROBE FOR THE INSPECTION OF SCREWS FOR NUCLEAR REACTOR PRESSURE VESSELS

The invention relates to a method for the testing or inspection of screws by means of an eddy current test probe with at least one coil through which high-frequency alternating current flows, the coil being disposed in an insulating material body, one contact surface of which is guided along the threads of the screw. The invention also relates to an eddy current test probe for the execution of the method.

Figure 1:
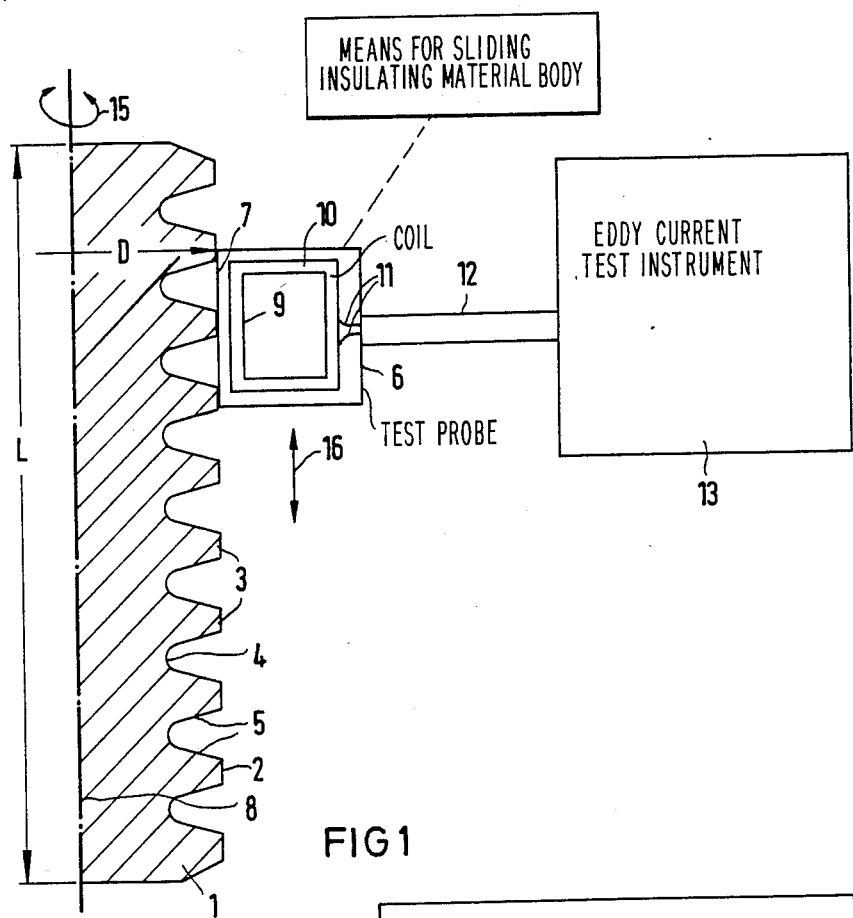

Such an eddy current test probe is known from German Published, Prosecuted Application DE-AS 28 17 574. In the embodiment of FIG. 1 of the German application, the device is used for the inspection of planar surfaces, the insulating material body is formed of plastic and the contact surface of the planar workpiece surface is also planar. The diameter of the cylindrical coils which are mutually parallel, coaxial and perpendicular to the contact surface, is 10 mm, and the spacing thereof should be in the order of magnitude of the diameter.

FIGS. 4 and 5 of the German application also illustrate the inspection of incisions such as threads or thread turns. In this case, the coils are no longer positioned parallel to each other on the same axis, but instead are in one plane, one behind the other in a wedge-shaped insulating material body which engages the thread. A magnitude of 4 to 5 mm is mentioned for the coil diameter. The coil spacing is to be 2 mm. For testing, the coils with the insulating material body are moved in the direction of the threads or thread turns. This detects faults in the thread base in particular. The disadvantage of such a device is that it does not test the entire thread region and the testing is quite time-consuming.

It is accordingly an object of the invention to provide a method and eddy current test probe for the inspection of screws, which overcomes the hereinafore-mentioned disadvantages of the heretofore-known devices of this general type, and to do so in such a manner that inspections of setscrews on reactor pressure vessels can be carried out particularly well. Through the use of the invention, faults in the entire thread area and not only in the thread base of the setscrews are reliably located. In addition, a shortening of the conventional testing time is desired because a strong radiation exposure at the reactor pressure vessel limits the working time of inspection personnel.

With the foregoing and other objects in view there is provided, in accordance with the invention, a method for the inspection or testing of screws with an eddy current test probe including an insulating material body having a linear contact surface and at least one coil disposed in the body, which comprises orienting the coil transverse to threads to thread turns of a reactor pressure vessel setscrew to be inspected, feeding high-frequency alternating current through the at least one coil, generating a coil field covering at least two threads, and guiding the linear surface along and above the threads.

The invention achieves simultaneous coverage of several threads or thread turns of setscrews on reactor pressure vessels, while covering the flanks or lateral surfaces of the threads in their entirety and yet also covering the thread base with sufficient accuracy. It has been possible to provide by testing that reliable recognition of a groove that is 3 mm deep which meets the test specifications is obtained, even when incipient cracks are perpendicular to the direction of stress. At the same time, the testing of the setscrews can be extended to cover the thread sections as well as a shaft and possibly shaft transitions, in one operation. This results in significant time saving over conventional tests which required different eddy current test probes for each of these purposes.

In accordance with another mode of the invention, there is provided a method which comprises guiding the insulating material body along surface lines, tangents or generatrices of the setscrew, and rotating the setscrews while guiding the body.

Further in accordance with the objects of the invention, there is provided an eddy current test probe for inspecting screws, comprising an insulating material body having a linear contact surface to be guided along threads of a setscrew for a reactor pressure vessel, and at least one high-frequency a-c coil disposed in the body and oriented transverse to the threads for generating a coil field covering at least two threads, the contact surface being unidimensionally curved according to the outside diameter of the screw.

In the invention, the coils do not have to be round. On the contrary, flattened coils may be used, as is known from the abovementioned German application.

In accordance with an added feature of the invention, the coil has a substantially straight section in the vicinity of the contact surface. This straight section has a length substantially between 12 and 30 mm.

In accordance with an additional feature of the invention, the coil has a rectangular or square cross section.

In accordance with again another feature of the invention, the screw is a setscrew for a reactor pressure vessel.

In accordance with a concomitant feature of the invention, there is provided an eddy current test probe for inspecting screws, comprising an insulating material body having a linear contact surface to be guided along threads of a setscrew for a reactor pressure vessel, and at least one high-frequency a-c coil disposed in the body and oriented transverse to the threads for generating a coil field covering at least two threads, the contact surfaces being planar. In this way, the probe can be employed for setscrews of different diameter.

Other features which are considered as characteristic for the invention are set forth in the appended claims.

Although the invention is illustrated and described herein as embodied in a method and current eddy test probe for the inspection of screws, it is nevertheless not intended to be limited to the details shown, since various modifications and structural changes may be made therein without departing from the spirit of the invention and within the scope and range of equivalents of the claims.

Figure 2:
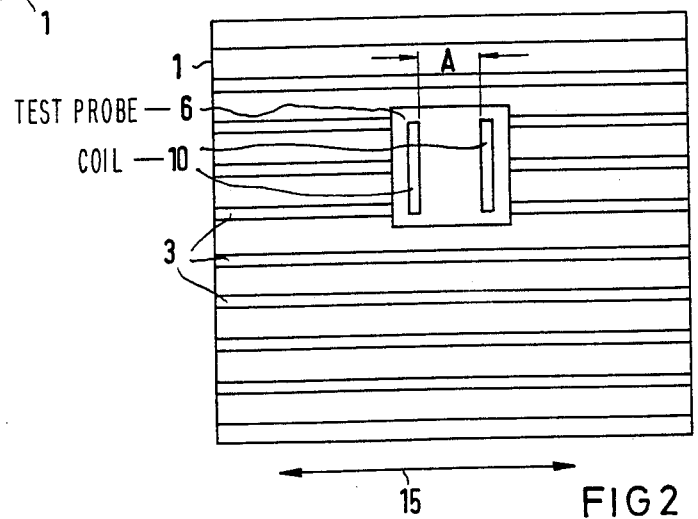

The construction and method of operation of the invention, however, together with additional objects and advantages thereof will be best understood from the following description of specific embodiments when read in connection with the accompanying drawings, in which:

FIG. 1 is a fragmentary, diagrammatic, partially cross-sectional, side-elevational view of the invention; and FIG. 2 is a developed projection of a setscrew as seen during the inspection performed according to the invention.

Referring now to the figures of the drawings in detail and first, particularly to FIG. 1 thereof, it is seen that a test specimen which is a setscrew or stud bolt 1, is used to fasten the cover of reactor pressure vessels. The diameter D of the setscrew 1 may be 220 mm and its length L may be 2500 mm. Thread turns 3 of an M 220×8 thread are machined into the cylindrical outer periphery of the setscrew 1. The thread base 4 and tooth flanks or lateral surfaces 5 are of particular importance for the testing of the soundness of the setscrew 1.

A test probe 6 serves for the eddy current inspection of the setscrew 1. The probe 6 is a cuboid plastic part with a square cross section having edges that are 50 mm long, for instance. The plastic part, which is made of Plexiglass or Teflon, forms a contact surface 7 facing the setscrew 1, in the shape of a 50 mm ×50 mm cylindrical surface. As may be seen, this surface which is unidimensionally curved at a 110 to 112 mm radius of curvature, is oriented parallel to an axis 8 of the setscrew and touches the cylindrical contoured surface of the thread in the vicinity of a coil section 9 along a surface line or generatrix.

The straight coil section 9 is part of two eddy current coils 10 having square cross sections, which are bound in the plastic part 6 in such a way as to be side by side and mutually parallel, as seen in FIG. 2. The length of a side of the square cross section of the coils 10 is is 25 mm. Thus, this length also applies to the straight section 9 adjacent a contact surface 7 of the test probe 6, so that in the illustrated embodiment, the magnetic field of the coils 10 covers three adjacent turns of the thread 3. The coils are formed of many windings of a copper wire which may be 0.05 to 0.5 mm thick. As FIG. 2 shows, the coils 10 are mutually spaced apart by a distance A, which is in the order of magnitude of the length of the coils. Leads 11 of the coils extend from the insulated part 6 to a common connecting cable 12, which establishes the connection to an eddy current test instrument 13.

During the eddy current test, one of the two coils 10 is supplied with a high-frequency alternating curernt which may be 25 or 100 kHz. The eddy current test instrument then evaluates the voltages in the other coil obtained by magnetic coupling through the setscrew 1, as is known in the art. During this process, the setscrew or bolt 1 performs a rotary motion about its axis 8, as indicated by an arrow 15. At the same time, the test probe 6 is moved parallel to the axis 8, as indicated by an arrow 16. This results in a helical test path which covers several turns of the thread in one operation, from the outer edge of the thread to the thread base 4.

Besides testing the thread area, it is also possible with the new test probe to test cylindrical shaft areas and transitions on setscrews for reactor pressure vessels, in a single operation. Compared to conventional inspections, this results in a reduction of the inspection time to less than half. In view of the radiation exposure in the vicinity of the reactor pressure vessel, this is a significant improvement.

We claim:

1. Eddy current probe for inspecting screws for nuclear reactor pressure vessels, comprising at least one coil disposed with its axis perpendicular to the direction of the axis of the screw, the coil having a high frequency alternating current flowing through it for creating a magnetic high frequency alternating field; an eddy current test instrument connected to the coil for evaluating impedance changes caused by irregularities in the screw threads; wherein said coil has at least one straight coil section which is oriented parallel with the axis of the screw and has dimensions such that said magnetic field completely covers at least two screw threads; and including an insulating material body for containing the coil; said insulating material body having a planar contact surface matching, for closely contacting, the cylindrical contoured surface of the screw; and means for sliding said insulating material body axially along the contoured surface of the screw.

2. Eddy current test probe according to claim 1, wherein said at least one coil in the vicinity of said contact surface has a length substantially between 12 and 30 mm.

3. Eddy current test probe according to claim 1, wherein said coil has a substantially straight section in the vicinity of said contact surface.

4. Eddy current test probe according to claim 2, wherein said coil has a substantially straight section in the vicinity of said contact surface.

5. Eddy current test probe according to claim 3, wherein said coil has a rectangular cross section.

6. Eddy current test probe according to claim 4, wherein said coil has a rectangular cross section.

7. Eddy current test probe according to claim 5, wherein said coil has a square cross section.

8. Eddy current test probe according to claim 6, wherein said coil has a square cross section.

9. Eddy current test probe according to claim 1, wherein the screw is a setscrew for a reactor pressure vessel.

10. Eddy current probe for inspecting screws for nuclear reactor pressure vessels, comprising one coil disposed with its axis perpendicular to the direction of the axis of the screw, the coil having a high frequency alternating current flowing through it for creating a magnetic high frequency alternating field; an eddy current test instrument connected to the coil for evaluating impedance changes caused by irregularities in the screw threads; wherein said coil has at least one straight coil section which is oriented parallel with the axis of the screw and has dimensions such that said magnetic field completely covers at least two screw threads; and including an insulating material body for containing the coil; said insulating material body having a planar contact surface matching, for closely contacting, the cylindrical contoured surface of the screw; and means for sliding said insulating material body axially along the contoured surface of the screw.

11. Method for inspection of screws having thread turns with an eddy current test probe having at least one coil having at least one straight coil section and having high-frequency alternating current flowing through the coil whereby a magnetic alternating field is produced, the coil being disposed in an insulating material body having a linear contact surface being parallel with the straight coil section and matching the cylindrical contoured surface of the screw for guiding it along the threads of the screw, whereby impedance changes through the unevenness of the thread turns are registered and indicated in an eddy current test instrument, comprising the steps of: orienting the coil for testing setscrews on reactor pressure vessels with its straight coil section parallel with the axis of the setscrews, selecting the coil dimensions such that its field covers at least two thread turns and guiding the insulation material body with the linear contact surface along and proximal to the thread turns.

* * * * *